United States Patent [19]

Dattagupta

[11] Patent Number: 5,215,899

[45] Date of Patent: Jun. 1, 1993

[54] NUCLEIC ACID AMPLIFICATION EMPLOYING LIGATABLE HAIRPIN PROBE AND TRANSCRIPTION

[75] Inventor: Nanibhushan Dattagupta, Orange, Conn.

[73] Assignee: Miles Inc., Elkhart, Ind.

[21] Appl. No.: 569,991

[22] Filed: Aug. 23, 1990

Related U.S. Application Data

[63] Continuation-in-part of Ser. No. 434,372, Nov. 9, 1989, abandoned.

[51] Int. Cl.$^5$ .......................... C12P 19/34; C12Q 1/68
[52] U.S. Cl. ........................................ 435/6; 435/91;
435/172.3; 435/320.1; 435/805; 436/501;
436/508; 436/538; 436/815; 536/24.3;
536/24.31; 536/24.32; 935/2; 935/18; 935/19;
935/78; 935/88; 935/110
[58] Field of Search .................. 435/6, 91, 805, 172.3,
435/320.1; 436/501, 508, 538, 815; 536/27;
935/2, 18, 19, 78, 88, 110

[56] References Cited

U.S. PATENT DOCUMENTS

| 4,683,195 | 7/1987 | Mullis et al. ............................. 435/6 |
| 4,683,202 | 7/1987 | Mullis ..................................... 435/91 |

FOREIGN PATENT DOCUMENTS

| 0292802 | 11/1988 | European Pat. Off. . |
| 0310229 | 4/1989 | European Pat. Off. . |
| 0320308 | 6/1989 | European Pat. Off. . |
| 8810315 | 12/1988 | PCT Int'l Appl. . |
| 2125964 | 3/1984 | United Kingdom . |
| 8706270 | 10/1987 | World Int. Prop. O. . |

OTHER PUBLICATIONS

Cantor et al. (1980) Biophysical Chemistry, Part III (W. H. Freeman & Co., U.S.A.) p. 1183.
Jendrossek et al. (1988) J. of Bect., vol. 170, No. 11 pp. 5248-5256.
Walker et al. (1984) Biochem J. vol. 224, pp. 799-815.
La Fanci et al. (1989) Bioch. and Biophysical Res. Comm. vol. 159, No. 1, pp. 297-304.
Sriprakesh et al. (1989) Gene Anal. Tech., vol. 6, pp. 29-32.
Krupp et al. (1987) Febs. Lett. vol. 242, No. 2, pp. 271-275.
Nucleic Acid Probes (CRC Press, U.S.A., 1989) Ed., Symons pp. 21, 22, and 30.
Szybelski (1985) Gene, vol. 40, pp. 169-173.

Primary Examiner—Amelia Burgess Yarbrough
Assistant Examiner—Ardin H. Marschel
Attorney, Agent, or Firm—Andrew L. Klawitter

[57] ABSTRACT

Specific nucleic acid sequences are amplified through the use of a hairpin probe which, upon hybridization with and ligation to, a target sequence is capable of being transcribed. The probe comprises a single stranded self-complementary sequence which, under hybridizing conditions, forms a hairpin structure having a functional promoter region, and further comprises a single stranded probe sequence extending from the 3' end of the hairpin sequence. Upon hybridization with a target sequence complementary to the probe sequence and ligation of the 3' end of the hybridized target sequence to the 5' end of the hairpin probe, the target sequence is rendered transcribable in the presence of a suitable RNA polymerase and appropriate ribonucleoside triphosphate (rNTPs). Amplification is accomplished by hybridizing the desired target nucleic acid sequence with the probe, ligating the target sequence to the probe, adding the RNA polymerase and rNTPs to the separated hybrids, and allowing transcription to proceed until a desired amount of RNA transcription product has accumulated. The amplification method is particularly useful in assays for the detection of particular nucleic acid sequences.

40 Claims, 3 Drawing Sheets

HAIRPIN PROBE + SAMPLE NUCLEIC ACIDS

↓ HYBRIDIZE

(I)

↓ LIGATE (II)

↓ ADD POLYMERASE AND rNTPs

TRANSCRIPTION PRODUCTS

NUCLEIC ACID AMPLIFICATION EMPLOYING LIGATABLE HAIRPIN PROBE AND TRANSCRIPTION

CROSS-REFERENCE TO RELATED APPLICATIONS

This is a continuation-in-part of application Ser. No. 434,372, filed Nov. 9, 1989, now abandoned.

BACKGROUND OF THE INVENTION

The present invention relates to methods for anplifying nucleic acid sequences. In particular, the invention concerns methods for detecting the presence of a particular nucleic acid sequence with high sensitivity.

The detection of specific nucleic acid sequences is gaining rapid importance in a variety of fields, particularly in the field of medical diagnosis. Nucleic acid hybridization methods provide assays for detecting nucleic acid sequences of medical significance, such as DNA or RNA sequences indicative of genetic diseases, cancer, and bacterial and viral infections. Nucleic acid hybridization assays are based on the very specific base pairing that is found in hybrids of DNA and RNA. Base sequences of analytical interest appearing along a strand of nucleic acid can be detected very specifically and sensitively by observing the formation of hybrids in the presence of a probe nucleic acid known to comprise a base sequence that is complementary with the sequence of interest.

It is evident that for hybridization assays to attain their full analytical potential, methods for increasing the sensitivity of detection even further are needed. Considerable efforts have been applied to this aspect in recent years and a number of different approaches have been conceived and developed. Particularly promising are approaches based on the biochemical amplification of the target nucleic acid sequence or its complementary signal sequence. While detection systems each have their own sensitivity limits, biochemical systems have been developed which can make millions and millions of copies of the target or signal sequences thereby to extend the effective sensitivity limits of such detection systems by many orders of magnitude.

One such nucleic acid amplification method is that known as the polymerase chain reaction method, or PCR, which is described in U.S. Pat. Nos. 4,683,195 and 4,683,202. PCR employs a pair of specific oligonucleotide as primers for the two complementary strands of the double stranded form of a target sequence. The primers are chosen such that they form specific hybrids at the opposite 3' ends of the complementary target strands. Using a thermostable DNA polymerase, the primers are extended synthetically in correspondence with the target sequences. A thermal cycling process is required in order to form specific hybrids and, after extension, to denature the hybridized, extended strands for further primer hybridization and extension. Repeating the process several times results in a geometric amplification of the amount of the target sequences in the mixture.

A variation of PCR is the ligase chain reaction (LCR) described in European Patent Publication 320,308. This method requires at least four separate oligoprobes, two of which hybridize to opposite ends of the same target strand such that when they are hybridized to the target sequence their respective 3' and 5' ends are juxtaposed for ligation. The third and fourth probes hybridize with the first and second probes to form, upon ligation, fused probes which can be denatured and detected.

Another known amplification method is described in PCT Publication No. 88-10315 and will be referred to as the transcription amplification system or TAS. Similar methods are described in European Patent Publication No. 310,229 and PCT Publication No. 88-10315. As in PCR, TAS uses pairs of oligoprimers to hybridize with opposite ends of a desired target sequence. The primers are chosen such that the extension products, after either a single extension or multiple cycles as in PCR, comprise transcription promoter sites. In the presence of a suitable promoter specific polymerase and ribonucleoside triphosphates (rNTPs), the extension products are themselves further amplified by transcription.

The $Q\beta$ replicase ($Q\beta R$) method described in PCT Publication No. 87-06270 uses a specific RNA probe which is capable of specific transcription by a replicase enzyme. The method has linear reaction kinetics and requires the design and synthesis of RNA probes with replicase initiation sites.

While all of these methods yield amplification of a target nucleic acid sequence, none are without complexities which are undesirable for the general and unsophisticated user. Many of the prior art methods require multiple incompatible steps that can be accomplished only by cumbersome manual procedures or complex and expensive instruments for automating the many manipulations required. Further, many require the preparation of multiple sophisticated reagents which limits the ready application of the methods to different target sequences.

Unrelated to the above pursuits, there have been studies of a variety of synthetic and naturally occurring DNA and RNA structures and their functions. One such structure is that known as the hairpin in which self-complementary regions in a single polynucleotide hybridize under suitable conditions to form looped structures whose shape resembles a common hairpin. Such hairpin structures are known to occur naturally in many organisms, particularly in RNA secondary structures, however, their functional role is at this point not well established. The physical chemistry of hairpin structures has been described —Cantor and Schimmel, Biophysical Chemistry, Part III, p. 1183, W. H. Freeman & Co. (San Francisco 1980).

The literature on this subject is incomplete and contradictory. For example, there are predictions that hairpins may provide a transcription termination signal—Jendrossek et al, J. Bacteriol. 170:5248 (1988) and Walker et al, Biochem. J. 224:799 (1984). Hairpin structures resembling known rho dependent transcription termination signals have been observed following the unc operon and glms of *E. coli*. On the other hand, palindromic sequences capable of forming stable hairpin forms have been found around the transcription initiation site of beta amyloid precursor gene—La Fauci et al, Biochem. Biophys. Res. Commun. 159:297 (1989).

The use of hairpin structures in the synthesis of DNA from oligonucleotides and in the labeling of oligonucleotides is proposed in European Patent Publication 292,802 and by Sriprakash and Hartas, Gene Anal. Techn. 6:29-32 (1989). In addition, Krupp and Soll, FEBS Letters 212:271 (1987) and "Nucleic Acid Probes", ed. Symons (CRC Press, Bacon Raton, Fla., 1989) pp. 21 & 22, describe the use of a hairpin structure to make labeled RNA transcripts from an M13 vector/T7 RNA polymerase system.

SUMMARY OF THE INVENTION

The present invention provides a method and means for amplifying a particular nucleic acid sequence of interest (target sequence) by hybridization with and ligation to a probe which renders the target sequence transcribable, and accordingly, capable of providing multiple copies of complementary RNA. The probe has two principal parts, (1) a single stranded self-complementary sequence capable of forming, under suitable hybridizing conditions, a hairpin structure having a functional promoter region, and (2) a single stranded probe sequence extending from, and forming part of the same nucleic acid molecule with, the 3' end of the self-complementary sequence.

Under suitable hybridizing conditions, the self-complementary region of the probe forms a looped, self-hybridized structure commonly referred to as a hairpin loop, or simply, hairpin. The base sequence of the self-complementary region is selected such that upon formation of the hairpin with the target sequence ligated to the 5' end of the probe, a desired double stranded promoter sequence is formed operably linked to the ligated target sequence. Thus, the hairpin form of the probe ligated to the target sequence is transcribable in the presence of a suitable RNA polymerase and the required ribonucleoside triphosphates (rNTPs). The sequence of bases in the RNA transcription product will accordingly be complementary with the target sequence.

Transcription can be allowed to proceed for any desired length of time with the accumulated transcription product producing an amplification of the target sequence. Where the target sequence is of analytical interest, high sensitivity detection of the target sequence can be accomplished by amplifying the target in the manner of the present invention and then suitably detecting the accumulated transcription product. Any number of conventional approaches can be taken in order to detect the accumulated RNA transcription product.

For example, the rNTPs added for transcription can comprise a detectable label and, after separating resulting labeled transcription product from the unused labeled rNTPs, the label is detected in the separated product fraction. Another approach is to detect the transcription product by hybridization with a detectable nucleic acid probe and detecting the resulting hybrids in any conventional manner, e.g., using labeled probe or anti-hybrid selective antibody such as anti-DNA/RNA.

Amplification can be further increased by applying a secondary or second stage amplification of the generated RNA transcription product. A variety of methods are appropriate for this purpose, representative examples of which are described in more detail infra.

The present amplification method provides a number of significant advantages over the methods of the prior art. First, the present method requires, in its most general form, but a single probe component as opposed to the need for multiple probes, such as oligoprimers, in many of the prior art methods such as PCR, TAS, and LCR described above. Further, there is no need for time consuming and and cumbersome thermal cycling as with PCR and LCR. Unlike the QβR method described above, the present probe is a simple extended single stranded nucleic acid rather without complex tertiary structure. Other advantages will be evident to the worker in the field.

DESCRIPTION OF THE PREFERRED EMBODIMENTS

The Probe and Its Preparation

Figure 1:
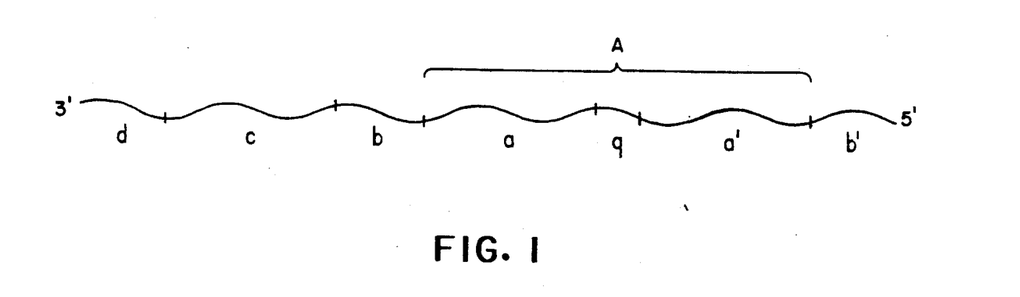
FIG. 1 is an illustration of a linear polynucleotide that under hybridizing conditions can form a hairpin structure useful in the present invention.
Figure 2:
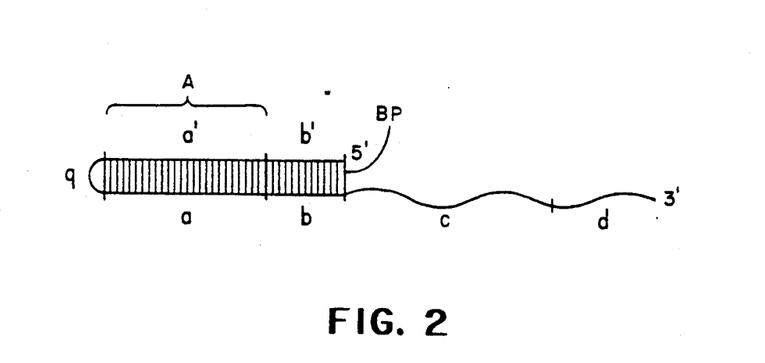
FIG. 2 is an illustration of the hairpin structure formed from the polynucleotide depicted FIG. 1 under hybridizing conditions.
Figure 3:
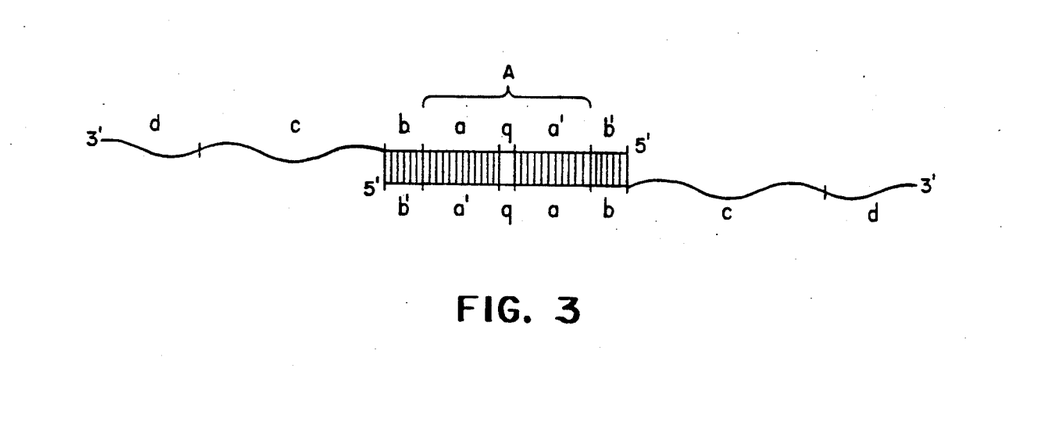
FIG. 3 is an illustration of a dimer structure that can form from the polynucleotide depicted in FIG. 1 under particular hybridizing conditions, which dimer functions equivalently to the hairpin structure depicted in FIG. 2.

The probe of the present invention comprises at least two principal parts joined together in a single polynucleotide. With reference to FIGS. 1-3 of the drawings, the first part is sequence of bases A that comprises self-complementary portions a and a' separated by a loop sequence q. Under hybridizing conditions, sequences a and a' self-anneal to form a looped, hairpin structure illustrated in FIG. 2 with the lines BP representing the base pair bonds formed between the self-complementary sequences. Sequences a and a' are selected in order that the resulting looped region A thereby comprises a functional promoter or transcription initiation site. The second principal part of the probe of the present invention is probe sequence c which is linked directly or through an intervening sequence b to the 3' end of promoter region A, and is selected to be hybridizable with a target sequence to be amplified or detected. As depicted in FIGS. 1-3, intervening sequence b is complementary with sequence b' flanking the 5' end of the self-complementary promoter region A. However, it will be recognized that flanking sequence b', if present, need only be long enough that, upon hybridization of probe sequence c with the target sequence, the 3' end of the target sequence is ligatable to the 5' end of such flanking sequence b'. Also, the probe can, in general, additionally comprise a 3' flanking sequence such as illustrated in FIGS. 1 and 2 as sequence d.

The hairpin form of the probe as depicted in FIG. 2 will enable transcription of a target sequence ligated to its 5' end to proceed in the presence of a cognate polymerase and the rNTPs required for 3'-5' transcription of the ligated target sequence and any intervening sequence b'. Depending upon the concentration of probe present and reaction conditions, a functionally transcribable dimeric form can also be formed (FIG. 3). Self-complementary region A can potentially hybridize not only with itself, but also with a second probe molecule to form a dimer through hybridization of complementary regions a and a' on separate probe strands. Such dimer, like the hairpin form depicted in FIG. 2, comprises a functional promoter in region A and, in the presence of cognate polymerase and rNTPs, will produce 3'-5' transcription of the ligated target sequence and any intervening sequence b'. Accordingly, when reference is made herein to the "hairpin form" of the present probe, it will be understood that the functionally equivalent dimeric form is intended as well.

The promoter formed by hybridization of hairpin region A of the probe can be any double stranded nucleic acid (e.g., DNA or RNA) sequence that corresponds with, and is recognized by, a polymerase enzyme which, as is known in the art, binds to the promoter and thereby initiates 3'-5' transcription. The length of the self-complementary sequences a and a' which form the promoter, while not critical to the operation of the present invention, will generally fall between about 7 and about 200 bases, and more commonly between about 10 and about 50 bases. In general, any promoter for which a suitable polymerase is known and available can be used in the present invention. Usually, the probe will be composed of DNA which is transcribable with DNA-dependent RNA polymerases, that is, polymerases that act upon a DNA template to produce RNA transcripts. However, RNA probes transcribable with RNA-dependent RNA polymerases (such as in certain viruses, e.g., retrovirus and picornavirus). Useful promoters include, among others, those recognized by RNA polymerases produced in bacteriophages, such as T7, T3, and SP6 phage.

Exemplary base sequences having promoter function with respect to such phage polymerases are (n=2 to 50; the sequences are shown in their self-hybridized, hairpin form and do not necessarily represent the minimum sequences required for promoter function):

The probe sequence c can be any sequence which is capable of hybridizing with the target sequence of interest. As is known in the art, the degree of homology between the probe and target sequences will depend upon the specific needs of the user. Where a high degree of specificity is needed or desired, perfect or near perfect homology may be required, such in the case of the detection of single base pair mismatches. However, in the normal case, a degree of nonhomology can be tolerated without sacrificing required specificity, amplification, or detection of the target sequence. Thus, the term "complementary" or "hybridizable" will be used herein to describe the desired or necessary degree of homology between the probe sequence and the target. The length of the probe sequence is, in general, not critical. However, in order to obtain rapid and strong hybridization with a selected target sequence, normally probe sequences of at least about 10 bases.

The loop sequence q in the probe which links the self-complementary, hairpin forming sequences a and a' can be of any composition and length so long as it does not substantially impede or inhibit the formation of the transcribable hairpin or dimer structures. Normally, loop sequence q will be selected to be substantially noncomplementary with itself, e.g., will be composed of a heteropolymeric or homopolymeric DNA or RNA such as a chain comprising only poly T, poly A, poly C, or poly G, or combinations, and will be at least about 2 bases long to allow sufficient steric freedom for loop formation. More usually, loop sequence q will be between about 4 and about 50 bases in length.

The probe is designed such that upon hybridization of a target sequence to probe sequence c, the 5' terminus of the probe (i.e., the 5' terminus of either self-complementary sequence a or any intervening sequence b) is ligatable to the 3' end of the target sequence. In this way, the target sequence becomes operably linked, as is known in the art, to the 5' end of the promoter. Thus, upon initiation of transcription, the sequences extending from the 5' end of the promoter are functionally transcribed by the polymerase to form RNA transcripts which comprise a sequence complementary to the target sequence. As indicated above, the probe sequence c can be separated by an intervening sequence b providing that upon ligation of a target sequence to the 5' end of the probe, corresponding intervening sequence b' retains operable linkage with the probe sequence, e.g., it does not contain a transcription termination site, is so long as to significantly reduce the efficiency of transcription of the probe sequence, or introduces significant nonspecific hybridization. In certain situations it will be desirable to include such an intervening sequence for stability or detection purposes. As mentioned above, where intervening sequences b and b' are present, it will be generally preferred that they be exactly complementary and thus will hybridize in the hairpin form to position the 5' end of the probe exactly matching with the opposing 5' end of the probe sequence. Upon hybridization of the target sequence, the 3' end thereof becomes efficiently positioned for ligation to the 5' end of the probe. However, it is also possible that intervening sequence b' is wholly or partially noncomplementary to intervening sequence b and may even be of greater length than intervening sequence b. In such case, it is only necessary that intervening sequence b' be long enough for, and not substantially noninhibitory towards, ligation of the 3' end of a target sequence that is hybridized to probe sequence c to the 5' end of the probe of the present invention. It has also been found that the efficiency of transcription can be dependent upon the sequence presented in the first few (e.g., 3 to 5) nucleotides in the transcribable sequence. In particular, it has been found that highly efficient transcription using T7 RNA polymerase can be attained where the initial sequence is CCCTC.

The probe can also comprises a flanking sequence at its 3' end. Sequence d flanking the 5' terminus will be transcribed to an extent dependent upon the efficiency of the RNA polymerase used and the conditions of transcription. In certain situations such flanking sequence can be used to advantage in separation or detection.

The probe of the present invention can be prepared by any suitable method. Such methods, in general, will include oligonucleotide synthesis and cloning in a replicable vector. Methods for nucleic acid synthesis are well known in the art. For example, in "Oligonucleotide Synthesis: A Practical Approach", ed. M. J. Gait, IRL Press (Oxford 1984) there are described several different methods of oligonucleotide synthesis and purification and analysis of resulting products. In an automated synthesizer, one starts with a 5'-protected, immobilized (through the 3'-hydroxyl) nucleoside residue. After 5'-deprotection, a phosphodiester linkage is introduced by reaction with a 3'-phosphoramidite, 5'-protected nucleoside residue. The phosphite linkage is then oxidized to a stable linkage and the process is cycled with desired nucleoside residues for the sequence to be synthesized. In place of this phosphite triester phosphotriester method, one can also use a solid phase approach. Also, the synthesized nucleic acid can be further modified by synthetic methods (e.g., as described in U.S. Pat. No. 4,818,681). Cloning of nucleic acids in an amplifying vector is also well known in the art (see Maniatis et al, Molecular Cloning, Cold Spring Harbor (1982). When cloned in a double-stranded vector, strand separation may be necessary in order to use the product as a probe.

Target Amplification Methods

The first step in amplifying a particular target nucleic acid according to the present method is the hybridization of such target with the transcribable probe in a suitable liquid mixture. Such hybridization will be performed under suitable conditions well known in the art.

The sample suspected or known to contain the intended target nucleic acid may be obtained from a variety of sources. It can be a biological sample, a food or agricultural sample, an environmental sample, and so forth. In applying the present method to the detection of a particular nucleic acid sequence in the assistance of medical diagnosis, the test sample can be a body fluid or exudate such as urine, blood, milk, cerebrospinal fluid, sputum, saliva, stool, lung aspirates, throat or genital swabs, and the like. As discussed elsewhere in more detail herein, the target nucleic acid can be RNA or DNA.

It will be understood that it is generally required to treat sample nucleic acids for the purpose of forming suitable fragments comprising the target sequence that will hybridize and be ligatable to the probe. Further, in certain circumstances, it will be necessary or desirable to treat the test sample to release and/or extract the target nucleic acid for hybridization, and/or, when the target nucleic acid is presented in double stranded form, to denature and render such in hybridizable single stranded form by means well known in the art.

Fragmentation of sample nucleic acids is normally necessary to enable ligation of the target sequence to the probe. Such fragmentation can be accomplished by random or specific means. Specific restriction endonucleases can be used for this purpose, as well as more general DNAses, phophodiesterases, exonucleases and endonucleases. These processes are well known in the art. In some cases, further processing of the fragmented sample nucleic acids will be necessary to produce ligatable sites. For example, DNAse I degrades DNA to produce 5' phosphorylated residues. Thus, DNA that has been degraded by other methods cam be treated with DNAse I to produce ligatable fragments.

The use of restriction enzymes for the purpose of fragmentation is normally most advantageous. Degradation of nucleic acids with restriction enzymes produce fragments having defined termini and ligatable sites. For example, in the case of DNA ligation using a specific enzyme such as T4 DNA ligase, it is desirable that a phosphorylated 5' end of one fragment be juxtaposed with a 3' hydroxyl group on the other fragment. This can be readily accomplished by restriction enzyme digestion. As is the case in performing the present method, the efficiency of ligation is greatest when both fragments to be ligated are in double stranded form at the ligation site.

Any of the many known restriction enzymes can be used in the present invention depending upon the sequence selected at and flanking the ligation site. The sequence specificity of restriction enzymes provides flexibility in designing the probe sequence comprised in the hairpin probe of the present invention. For example, DdeI polymorphism of the human sickle mutation of the beta globin gene can be identified using a DdeI digested human DNA sample. The probe sequence can be designed to encompass the site of the mutation such that a DdeI cut fragment will, upon hybridization, align its 3' end with the 5' end of the hairpin probe. Such hybridized DNA fragment will be efficiently ligatable to the probe and thereby rendered transcribable. On the other hand, DNA in which the mutation is absent will not be digested although it will hybridize to a substantial extent. However, ligation will proceed much less efficiently because of improper orientation of the ligation partners. Another example using restriction enzymes is the detection of sequences of *Chlamydia trachomatis*. The sample nucleic acids can be digested with restriction enzymes (SstI to cut the plasmid DNA once or Hind III to cut it several times, Black et al., Current Microbiology (1989) 19:67-74) in such a way that the plasmid DNA of the organism is also digested to produce multiple fragments. Probes corresponding to all such fragments can be hybridized, ligated, and transcribed separately or simultaneously. After transcription, the RNA can be analyzed by hybridization with a single plasmid DNA probe.

DNA can also be degraded by a variety of other means, such as the use of the following types of reagents: EDTA-Fe(II), Stroebel et al. (1988) J. Am. Chem. Soc. 110:7927, and Dervan (1986) Science 232:464; Cu(II)-phenanthroline, Chen and Sigman (1987) Science 237:1197; class IIS restriction enzyme, Kim et al (1988) Science 240:504; hybrid DNAse, Corey et al (1989) Biochem. 28:8277; bleomycin, Umezawa et al (1986) J. Antibiot. (Tokyo) Ser. A, 19:200; neocarzinostatin, Goldberg et al (1981) Second Annual Bristol-Myers Symposium in Cancer Research (Academic Press, New York) p. 163; and methidiumpropyl-EDTA-Fe(II), Hertzberg et al (1982) J. Am .Chem. Soc. 104:313.

Figure 4:
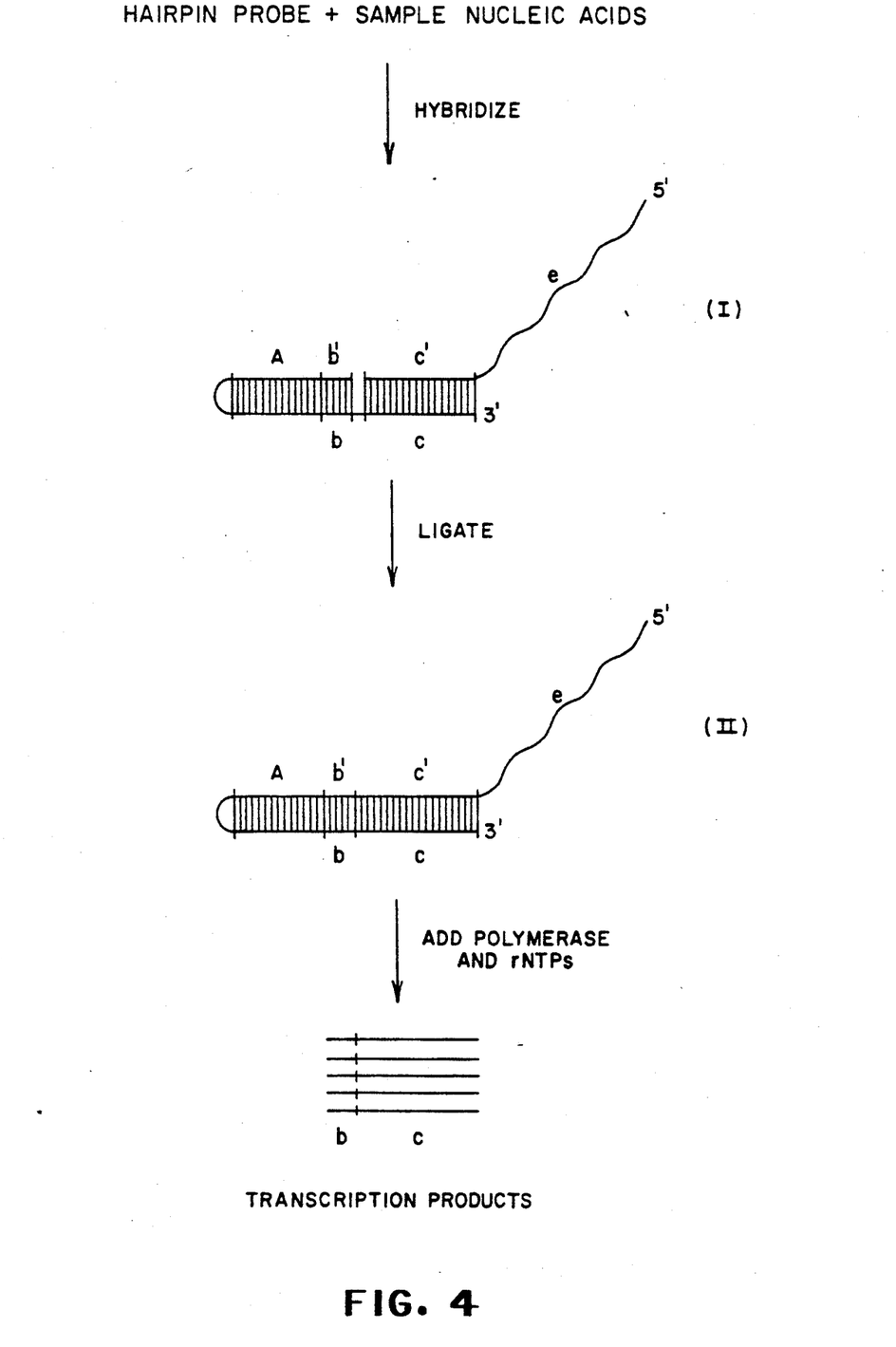
FIG. 4 is a diagram illustrating the use of a probe of the present invention in amplifying a target nucleic acid sequence.

The amplification method of the present invention is illustrated in the diagram of FIG. 4. Hybridization of the present hairpin probe and the target sequence present in a sample of nucleic acids produces hybrids (I) in which the probe sequence c in the probe is hybridized with its complementary target sequence c'. In FIG. 4, intervening sequences b and b' in the probe are depicted as being complementary to one another, which, as discussed herein elsewhere, is not considered critical, but is generally preferred. After hybridization, the juxtaposed 5' and 3' ends of probe sequence b' and target sequence c', respectively, are ligated to yield ligated hybrid products (II). With the addition of the polymerase and rNTPs, transcription proceeds with the generation of multiple RNA transcripts having the combined sequence bc.

Transcription is initiated by addition of polymerase and the required rNTPs to the liquid mixture that contains the hybrids comprising the ligated, transcribable target sequence. Under suitable conditions, the synthesis of RNA transcripts will proceed in a continuous manner providing that sufficient amounts of rNTPs are present. Normally, a ribonuclease inhibitor will be included in the transcription reaction mixture in order to avoid undesirable degradation of RNA transcripts by any ribonuclease contamination. Transcription is allowed to proceed for a predetermined period of time or until a detectable or desirable amount of RNA transcript has accumulated. The amount of RNA transcript produced in a given period of time will be proportional to the amount of target sequence present in the original sample. The accumulated transcription product thus serves as an amplification of the target sequence. Transcription can then be terminated by any conventional means such as inactivation of the polymerase or removal of reactants from the mixture.

Further amplification of the RNA transcription products can be accomplished in a number of ways, for example, by the use of replicases such as Q$\beta$ replicase or replicase from brome mosaic virus. Also, a separate set of hairpin probe/second probe pairs can be used comprising (1) a transcribable hairpin probe (constructed with a self-annealing, promoter-containing region as in the present probe but with a transcribable probe region complementary with the RNA transcripts extending from the 5' end, rather than from the 3' end as in the present probe) and (2) a second probe which hybridizes with an adjacent sequence in the RNA transcription product. After hybridizing the hairpin probe/second probe pairs to transcripts, the hybridized pair is ligated to form transcribable nucleic acids which themselves will produce additional RNA transcript in the presence of the polymerase. Further, the RNA transcripts can be produced to contain a site for immobilization (e.g., by use of ligand, e.g., biotin or hapten, modified rNTPs and immobilization of resulting transcripts by addition of an immobilized form of a ligand binding partner, e.g., avidin or an anti-hapten antibody, respectively), and after being separated from the mixture can be hybridized to a further probe to introduce a promoter site for further transcription. After a few cycles, more than a millionfold amplification is possible.

The following methods in particular are useful for providing a second stage amplification:

(1) Displacing probe from hybrid by RNA—The promoter probe is hybridized with its complementary DNA which is immobilized onto a solid support or hybridized to an immobilizable support. The immobilized or immobilizable support is brought into contact with the product RNA under conditions of specific hybridization. This releases the transcribable probe since RNA will hybridize instead of the DNA because of the stability difference between the RNA-DNA hybrid and DNA-DNA hybrid. After the first stage of transcription, the RNA polymerase activity is destroyed by heating before the mixture is reacted with the immobilized DNA hybrid support under conditions of strand displacement. For every molecule of RNA, one molecule of promoter probe will be produced under the most ideal conditions. By cycling the system it is possible to use RNA to produce more and more transcribable probes and hence secondary amplification of the system. For more effective strand displacement, branch migration can be utilized. In this manner, the displacing DNA molecule has on its 3' or 5' end an unhybridized single stranded region where a corresponding part of the RNA initiates RNA-DNA hybrid formation.

It has been assumed that a single strand branch migration phenomenon is involved in transcription of a double stranded DNA. A newly synthesized strand of RNA replaces a DNA strand of the same sequence. The migration rate of a single stranded branch is estimated to be faster than 1,000 base pairs per second. A double stranded branch migration has also been described. This process is about 6,000 base pairs per second at 37° C. (Biophysical Chemistry, Cantor & Schimmel, Freeman publication, San Francisco, 1980, vol. III, pp. 1238-1239). From this information it can be easily estimated that a 20 base branch migration displacement should be a very rapid process without any high temperature treatment.

(2) Displacing one strand of the probe—This method is similar to the previous method except that the released probe is not the complete probe, but rather one strand of the probe with one strand of the promoter. Only addition of the other strand makes it transcribable.

(3) Displacing ligatable linker—This method is also similar to the previous methods, however, the released fragment acts as a linker for the ligation of two portions of the promoter probes.

(4) RNA mediated ligation—This method involves the use of RNA product to form a bridge over which ligation of two DNA fragments can occur and is characterized by the advantage of being capable of being performed in solution.

(5) Capture recycling—This method uses ligand-modified (e.g., biotinylated) RNA product of the first transcription as the capturing agent for the promoter probes. At the time of the initial transcription, biotinylated UTP is mixed with the other nucleoside triphosphates for the initial transcription. The biotinylated RNA is then either captured before or after mixing with the complementary promoter probe. When the biotinylated RNA is captured, the first interaction with the complementary DNA promoter is carried out on the solid support. The biotinylated RNA-DNA hybrid is then used for transcription to produce more RNA. If the transcription becomes inefficient from such a hybrid, heat or alkali treatment to release DNA from the hybrid can be carried out before transcription. A similar method can also be performed by using anti-RNA/DNA hybrid antibody capture reaction and dispensing with the step of biotinylating RNA.

(6) RNA mediated copying—This method creates a promoter site by using the transcript as a primer. The primer extension product acts as the transcribable signal. A sequence complementary to the RNA product is cloned into a single stranded phage vector e.g., M13. The transcript is allowed to react with such M13 DNA and the hybrid is then extended using a DNA polymerase and deoxynucleoside triphosphates some of which are labeled for the identification of the product. This process can also produce transcribable sequences for further amplification.

An identical procedure can be followed via a synthetic oligonucleotide instead of a cloned DNA as the template for extension of the transcription product RNA primers.

Promoter-containing DNA is hybridized with the product RNA, extended by using a DNA polymerase and then extended product is transcribed. Starting single stranded RNA does not transcribe. The final product is analyzed by capture with a specific immobilized probe. This process can be adjusted to make as much amplification as needed for a sensitive analysis.

(7) Displaced DNA mediated copying—This method is the same as the previous method except that it uses displaced DNA as the primer for the extension to produce transcribable products.

(8) Immobilized oligo mediated capture—In this method, an oligonucleotide (e.g., half the size of the intact transcript) is immobilized onto a solid support, the product RNA is captured by hybridization, and the residual unhybridized portion of the RNA is then used to capture a transcribable hairpin probe.

(9) Use of RNA dependent RNA polymerases—In this method, the initial probe is modified to carry a sequence of single or double-stranded DNA which after transcription produces RNA specific for further amplification by an RNA dependent RNA polymerase (e.g., QB replicase). This sequence is on the 5' end of the probe. The product RNA is used for further amplification without secondary processing (see PCT Publication 88-10315).

Detection Methods

The method by which the synthesized and accumulated RNA transcripts are detected is dependent principally upon the desires and needs of the user. A wide variety of methods are known and will be developed in the future which can be applied to the present invention. By way of example only, a few methods will be described in detail herein. Principally, these methods are based on the production of labeled transcription product or on hybridization of the transcription product with detection of the resulting hybrids.

(1) Synthesis of labeled-RNA transcripts—The addition of rNTPs, one or more of which comprise a detectable label, to the transcription mixture will result in the synthesis of RNA transcripts that also comprise the detectable label. Substances which serve as useful detectable labels are well known in the art and include radioactive isotopes, e.g., $^{32}P$, $^{3}H$, $^{125}I$, and $^{14}C$, fluorescers, chemiluminescers, chromophores, and the like, as well as ligands such as biotin and haptens which, while not directly detectable, can be readily detected by reaction with labeled forms of their specific binding partners, e.g., avidin and antibodies, respectively.

(2) Detection by hybridization with labeled probe—This approach relies upon a further hybridization step for the detection of the RNA transcripts. A variety of methods are known for the preparation of probes which comprise labels that are directly or indirectly detectable. The labels can be any of the same materials mentioned immediately above.

(3) Detection by hybridization and use of anti-hybrid reagent—The detection probe can also be selected in a manner such that the hybrids formed with the RNA transcripts are unique in the mixture and thereby selectively detectable through the use of anti-hybrid reagents. A variety of anti-hybrid antibodies are known in the literature, including anti-DNA/RNA and anti-RNA/RNA antibodies (U.S. Pat. No. 4,833,084 and European Patent Publication No. 163,220), anti-DNA/DNA antibodies (U.S. Pat. No. 4,623,627), and antibodies to intercalation complexes (U.S. Pat. No. 4,563,417). The anti-hybrid antibody will advantageously be modified to contain a detectable label as above.

(4) Detection of RNA transcripts—The transcription products themselves can be detected in solution by separating RNA from the mixture, or by first destroying unreacted rNTPs with phosphatases, and then adding reagents that produce a detectable response to RNA, such as the bioluminescent system involving reaction with polynucleotide phosphorylase, pyruvate kinase and firefly luciferase (e.g., as described by C. P. H. Vary (1987) Nucleic Acids Res. 15:6883–6897).

Of course, since the transcription system can be designed to produce transcripts of a specified size, in such case they can be readily identified by size resolution methods such as gel electrophoresis.

The present invention will now be illustrated, but is not intended to be limited, by the following examples.

EXAMPLE 1

Ligation of probe to complementary oligonucleotide and transcription

This example demonstrated that a sample sequence after hybridization and ligation to a probe of the present invention will provide RNA synthesis by transcription.

The oligonucleotides HNT and CNT shown below were synthesized in an Applied Biosystems (Foster City, Calif., U.S.A.) Model 380 B oligonucleotide synthesizer using the supplier's reagents.

CNT: 3'-CCTCTTCAGACGGCAATG-5'

HNT, after gel electrophoretic purification was phosphorylated at its 5' end using polynucleotide kinase according to the method described in Maniatis et al (1982) Molecular Cloning, Cold Spring Harbor, p. 122. The kinased HNT was then hybridized with CNT at 37° C. for 5 minutes and then 100 units of T4 DNA ligase (Boehringer Mannheim, Indianapolis, Ind., U.S.A.) and ATP (10 mM final concentration) were added. The ligation reaction was carried out by incubating the mixture at 37° C. for 2 hours. HNT and CNT amounts were 20 ng each as the starting material.

Figure 5:
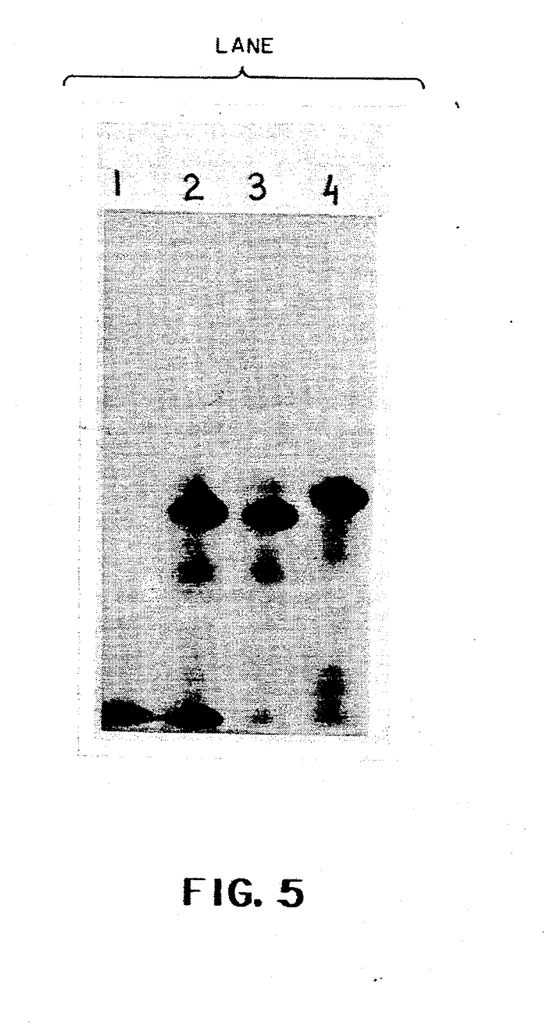
FIG. 5 shows an autoradiogram of a polyacrylamide gel demonstrating transcription of the ligation products produced from a probe of the present invention.

After ligation, the enzyme was inactivated either by heating at 100° C. or by phenol extraction and ethanol precipitation. The ligated product was then transcribed by adding 1 mM each of ATP, CTP, GTP, and UTP and 2 microcuries of alpha $^{32}P$ labeled UTP (3000 Ci per mM from Amersham, Arlington Heights, Ill., U.S.A.) and 20 units of T7 RNA polymerase (Pharmacia, Milwaukee, Wis., U.S.A.). The reaction was then incubated at 37° C. for 2 hours. The products were analyzed on a 20% denaturing polyacrylamide gel. The results are shown in FIG. 5 and demonstrate that the ligation process produces transcribable product.

EXAMPLE 2

Ligation in the presence of excess human DNA

A ligation identical to that in Example 1 was carried out in the presence of 1 to 10 micrograms of DNA extracted from human blood. The results are shown in FIG. 5 of the drawings as a picture of an electrophoresis gel autoradiogram. Lane 1 is kinased HNT as the template for transcription. Lanes 2 and 3 are digested HNT and CNT as templates, with lane 2 being unpurified material and lane 3 being material that was phenol extracted after ligation. Lane 4 is a positive control provided by a transcribable form of a hairpin probe.

EXAMPLE 3

Detection of a target sequence

A sample of plasmid DNA pss737 containing an insert of human betaglobin gene (see European Patent Publication 130,515) was digested with DdeI restriction enzyme to produce compatible ends for ligation with HNT. The digested DNA was then heated at 100° C. for five minutes for denaturation. The denatured sample was then hybridized with the HNT oligonucleotide probe, ligated at 37° C. for 2 hours, and transcribed as in Example 1. The gel electrophoretic analysis indicated the formation of a major RNA product approximately 200 nucleotides long.

WHAT IS CLAIMED IS:

1. A nucleic acid probe comprising (1) a single stranded self-complementary sequence capable of forming, under hybridizing conditions, a hairpin structure having a functional promoter region, and (2) a single stranded probe sequence extending from the 3' end of said self-complementary sequence, whereby upon hybridization of a target sequence complementary to said probe sequence and ligation of the resulting hybridized target sequence to the 5' end of the hairpin-forming self-complementary sequence, said target sequence is transcribable in the presence of an RNA polymerase and required ribonucleoside triphosphates under said hairpin-forming hybridizing conditions.

2. The probe of claim 1 composed of DNA and wherein said polymerase is a DNA-dependent RNA polymerase.

3. The probe of claim 2 wherein said polymerase is T7, T3, or SP6 bacteriophage RNA polymerase.

4. The probe of claim 3 wherein said promoter region comprises the following phase sequence shown in its hairpin form:

for T7, $T_n$  ;

for T3, $T_n$  ;

or for SP6, $T_n$  ;

wherein $T_n$ represents a sequence of from 2 to 50 thymidine residues.

5. A method for amplifying a particular target nucleic acid sequence, comprising the steps of:
 (a) hybridizing said target sequence with a probe of claim 1 in a liquid mixture,
 (b) ligating the resulting hybridized target sequence to the 5' end of said hairpin-forming self-complementary sequence,
 (c) adding to the ligated hybrids said RNA polymerase and ribonucleoside triphosphates sufficient for transcription of said target sequence in the hybrids, and
 (d) allowing the resulting transcription of said target sequence to take place for a predetermined period of time to accumulate the resulting complementary RNA transcription product as an amplification of said target sequence.

6. The method of claim 5 wherein the target sequence is present in a nucleic acid that has been fragmented.

7. The method of claim 6 wherein such fragmentation has been accomplished with a restriction endonuclease enzyme.

8. The method of claim 6 wherein the target sequence is present in a nucleic acid found in a biological test sample.

9. The method of claim 5 wherein the resulting RNA transcription product is further amplified in a second stage amplification.

10. The method of claim 9 wherein said second stage amplification is accomplished by separating the resulting RNA transcription product from the reaction mixture, hybridizing such separated transcription product with a transcribable probe and transcribing said probe under hairpin-forming hybridizing conditions.

11. The method of claim 10 wherein the resulting RNA transcription product is separated from the reaction mixture by having transcribed hybridized probe in the presence of one or more rNTPs comprising a bindable ligand and by adding an immobilized form of a ligand binding partner.

12. The method of claim 11 wherein said bindable ligand is biotin or a hapten and wherein said ligand binding partner is avidin or an anti-hapten antibody, respectively.

13. The method of claim 10 wherein the resulting RNA transcription product is separated from the reaction mixture by adding an immobilized form of an anti-RNA/DNA antibody reagent.

14. The method of claim 5 wherein said polymerase is a DNA-dependent RNA polymerase.

15. The method of claim 10 wherein said polymerase is T7, T3, or SP6 bacteriophage RNA polymerase.

16. The method of claim 15 wherein said promoter region comprises the following base sequence shown in its hairpin form:

for T7, $T_n$  ;

for T3, $T_n$  ;

or for SP6, wherein $T_n$ represents a sequence of from 2 to 50 thymidine residues.

17. A method for detecting a particular target nucleic acid sequence in a test sample, comprising the steps of:
(a) hybridizing said target sequence in the test sample with a probe of claim 1 in a liquid mixture,
(b) ligating the resulting hybridized target sequence to the 5' end of said hairpin-forming self-complementary sequence,
(c) adding to the ligated sequences said RNA polymerase and ribonucleoside triphosphates sufficient for transcription of said target sequence in the hybrids,
(d) allowing the resulting transcription of said target sequence to take place for a predetermined period of time to accumulate the resulting complementary RNA transcription product, and
(e) detecting said accumulated RNA transcription product.

18. The method of claim 17 wherein the accumulated RNA transcription product is detected by transcribing said target sequence in the presence of ribonucleoside triphosphates which comprise a detectable label, separating resulting labeled transcription product from the labeled ribonucleoside triphosphates, and detecting the label in the separated labeled transcription product.

19. The method of claim 17 wherein the accumulated RNA transcription product is detected by hybridizing such product with a detectable nucleic acid probe and detecting the resulting hybrids.

20. The method of claim 19 wherein the detectable probe comprises a label.

21. The method of claim 19 wherein the hybrids formed between the RNA transcription product and the detectable probe are detected by binding of a anti-hybrid selective antibody reagent.

22. The method of claim 21 wherein said hybrids are DNA/RNA hybrids and said antibody reagent is selective for binding DNA/RNA hybrids.

23. The method of claim 17 wherein the target sequence is present in a nucleic acid that has been fragmented.

24. The method of claim 23 wherein such fragmentation has been accomplished with a restriction endonuclease enzyme.

25. The method of claim 23 wherein the target sequence is present in a nucleic acid found in a biological test sample.

26. The method of claim 17 wherein the resulting RNA transcription product is further amplified in a second stage amplification.

27. The method of claim 26 wherein said second stage amplification is accomplished by separating the resulting RNA transcription product from the reaction mixture, hybridizing such separated transcription product with a transcribable probe, and transcribing said probe under hairpin-forming hybridizing conditions.

28. The method of claim 27 wherein the resulting RNA transcription product is separated from the reaction mixture by having transcribed hybridized probe in the presence of one or more rNTPs comprising a bindable ligand and by adding an immobilized form of a ligand binding partner.

29. The method of claim 28 wherein said bindable ligand is biotin or a hapten and wherein said ligand binding partner is avidin or an anti-hapten antibody, respectively.

30. The method of claim 27 wherein the resulting RNA transcription product is separated from the reaction mixture by adding an immobilized form of an anti-RNA/DNA antibody reagent.

31. The method of claim 17 wherein said polymerase is a DNA-dependent RNA polymerase.

32. The method of claim 31 wherein said polymerase is T7, T3, or SP6 bacteriophage RNA polymerase.

33. The method of claim 32 wherein said promoter region comprises the following base sequence shown in its hairpin form:

for T7, for T3, or for SP6, wherein $T_n$ represents a sequence of from 2 to 50 thymidine residues.

34. A reagent kit for use in amplifying a particular nucleic acid sequence, comprising:
(1) a nucleic acid probe of claim 1 which, upon hybridization with and ligation to said target sequence, is transcribable in the presence of an RNA polymerase and ribonucleoside triphosphates, and
(2) said RNA polymerase.

35. The kit of claim 34 which additionally comprises the ribonucleoside triphosphates required for transcription of the probe in the presence of the RNA polymerase.

36. The kit of claim 34 which additionally comprises a restriction endonuclease enzyme capable of fragmenting nucleic acids comprising said target sequence.

37. The kit of claim 36 wherein the target sequence is present in a nucleic acid found in a biological test sample.

38. The kit of claim 34 wherein said polymerase is a DNA-dependent RNA polymerase.

39. The kit of claim 34 wherein said polymerase is T7, T3, or SP6 bacteriophage RNA polymerase.

40. The kit of claim 39 wherein said promoter region comprises the following base sequence shown in its hairpin form:

for T7,

-continued for T3, T$_n$ ⌒ATTAACCCTCACTAAAGGGA-3'
         ⌣TAATTGGGAGTTAGCTTTCC-5'  ;

or

-continued for SP6, T$_n$ ⌒CATACGATTTAGGTGACACTATAG-3'
          ⌣GTATGCTAAATCCACTGTCATATC-5'  ;

wherein T$_n$ represents a sequence of from 2 to 50 thymidine residues.

* * * * *